(12) United States Patent
Nakano et al.

(10) Patent No.: US 8,588,502 B2
(45) Date of Patent: Nov. 19, 2013

(54) EVALUATION APPARATUS OF FLUORESCENCE POPULATION, EVALUATION METHOD OF FLUORESCENCE POPULATION AND COMPUTER READABLE STORAGE MEDIUM

(75) Inventors: Yoshitaro Nakano, Sunto-gun (JP); Yousuke Takahama, Tokushima (JP); Takeshi Nitta, Tokushima (JP)

(73) Assignees: Nikon Corporation, Tokyo (JP); The University of Tokushima, Tokushima (JP)

( * ) Notice: Subject to any disclaimer, the term of this patent is extended or adjusted under 35 U.S.C. 154(b) by 180 days.

(21) Appl. No.: 12/979,858

(22) Filed: Dec. 28, 2010

(65) Prior Publication Data
US 2011/0211741 A1    Sep. 1, 2011

Related U.S. Application Data

(63) Continuation of application No. PCT/JP2009/002901, filed on Jun. 24, 2009.

(30) Foreign Application Priority Data

Jul. 10, 2008    (JP) .................................. 2008-179765

(51) Int. Cl.
  *G06K 9/00*    (2006.01)
  *G06K 9/46*    (2006.01)
(52) U.S. Cl.
  USPC ............................ 382/133; 382/128; 382/195
(58) Field of Classification Search
  USPC .......................................... 382/133, 128, 195
  See application file for complete search history.

(56) References Cited

U.S. PATENT DOCUMENTS

| 5,885,840 | A | * | 3/1999 | Kamentsky et al. ............ 436/63 |
| 6,516,217 | B1 | | 2/2003 | Tsujita |
| 2002/0021355 | A1 | | 2/2002 | Utsui et al. |

(Continued)

FOREIGN PATENT DOCUMENTS

| JP | A-9-145593 | 6/1997 |
| JP | A-2001-17379 | 1/2001 |

(Continued)

OTHER PUBLICATIONS

International Search Report issued in International Application No. PCT/JP2009/002901 on Sep. 8, 2009 (with translation).

(Continued)

*Primary Examiner* — Bernard Krasnic
*Assistant Examiner* — Weiwen Yang
(74) *Attorney, Agent, or Firm* — Oliff & Berridge, PLC

(57) ABSTRACT

Statistical data of a fluorescence population is obtained easily with high accuracy. To achieve this, an evaluation apparatus of fluorescence population of the present application includes an input unit inputting a fluorescence observation image (If) of a fluorescence population and a transillumination observation image (It) having a same field of view as the fluorescence observation image, a first detecting unit (Mt) detecting, as a first area, an area in which a cellular image exists on the transillumination observation image being input, a setting unit (If') setting, as a reference area, an area corresponding to the first area on the fluorescence observation image being input, and an obtaining unit obtaining fluorescence intensity data of a fluorescence image from the reference area in the fluorescence observation image.

16 Claims, 11 Drawing Sheets

(56) References Cited

U.S. PATENT DOCUMENTS

| | | |
|---|---|---|
| 2002/0081014 A1 | 6/2002 | Ravkin |
| 2003/0081209 A1 | 5/2003 | Takahashi et al. |
| 2004/0001196 A1 | 1/2004 | Shibazaki et al. |

FOREIGN PATENT DOCUMENTS

| | | |
|---|---|---|
| JP | A-2002-51969 | 2/2002 |
| JP | A-2002-514304 | 5/2002 |
| JP | A-2002-257730 | 9/2002 |
| JP | A-2003-130866 | 5/2003 |
| JP | A-2006-194711 | 7/2006 |
| JP | A-2008-58249 | 3/2008 |

OTHER PUBLICATIONS

International Preliminary Report on Patentability issued in International Application No. PCT/JP2009/002901 on Feb. 8, 2011 (with translation).

* cited by examiner

EVALUATION APPARATUS OF FLUORESCENCE POPULATION, EVALUATION METHOD OF FLUORESCENCE POPULATION AND COMPUTER READABLE STORAGE MEDIUM

CROSS REFERENCE TO RELATED APPLICATION

This application is a Continuation Application of International Application No. PCT/JP2009/002901, filed on Jun. 24, 2009, designating the U.S., in which the International Application claims a priority date of Jul. 10, 2008, based on prior filed Japanese Patent Application No. 2008-179765, the entire contents of which are incorporated herein by reference.

BACKGROUND

1. Field

The present application relates to an evaluation apparatus of fluorescent object population, an evaluation method of fluorescent object population and a computer readable storage medium for evaluating a fluorescent object population such as a fluorescence-stained cell population.

2. Description of the Related Art

Conventionally, there has been known an evaluation apparatus of cell population (flow cytometer) in which a solution containing fluorescence-stained cell population is let to flow through a light-transmitting tube, a time change in a light emission amount of fluorescence is measured while irradiating excitation light to the tube, and statistical data regarding the fluorescence of the cell population is obtained based on the time change (Japanese Unexamined Patent Application Publication No. H 9-145593).

In recent years, there has been proposed an evaluation apparatus of cell population (hereinafter, called as "image cytometer") in which, instead of letting the solution containing cell population flow through the tube, a fluorescence microscope image of the cell population is obtained, and by performing image processing on the fluorescence microscope image, statistical data similar to the above data is obtained (Japanese Unexamined Patent Application Publication No. 2006-194711).

With the use of the image cytometer, there is no need to go through complicated measuring steps, and further, even detailed data regarding a structure in the cell can be obtained, which provides high availability.

However, a lot of noises are generated in the fluorescence microscope image, so that in the image cytometer, there is a need to distinguish between a cellular image and the noise, and to remove the latter before obtaining the statistical data. Actually, in the image cytometer disclosed in Japanese Unexamined Patent Application Publication No. 2006-194711, a bright spot whose brightness value exceeds a threshold value in the fluorescence microscope image is regarded as the cellular image, and a bright spot whose brightness value is equal to or less than the threshold value in the image is regarded as the noise, and the latter is removed.

However, the degree of staining of the individual cells varies, so that a fluorescence intensity is lowered depending on the cell, and the intensity sometimes becomes almost equal to a background level (noise level). Since such a cellular image is removed as the noise, an error occurs in the statistical data.

Note that if the threshold value is set low, a possibility of accidentally removing the cellular image is decreased, but, instead of this, there is increasing a possibility that a lot of noises remain, so that it is not possible to securely reduce the error in the statistical data.

SUMMARY

The present application is for solving the problems of the conventional art described above, and a proposition thereof is to provide an evaluation apparatus of fluorescent object population, an evaluation method of fluorescent object population and a computer readable storage medium capable of obtaining statistical data of the fluorescent object population easily with high accuracy.

An evaluation apparatus of fluorescent object population of the present application, including an input unit inputting a fluorescence observation image of a fluorescent object population and a transillumination observation image having a same field of view as the fluorescence observation image, a first detecting unit detecting, as a first area, an area in which a cellular image exists on the transillumination observation image being input, a setting unit setting, as a reference area, an area corresponding to the first area on the fluorescence observation image, being input, and an obtaining unit obtaining fluorescence intensity data of a fluorescence image from the reference area in the fluorescence observation image.

Further, an evaluation method of fluorescent object population of the present application, including an operation of inputting a fluorescence observation image of a fluorescent object population and a transillumination observation image having a same field of view as the fluorescence observation image, an operation of detecting, as a first area, an area in which a cellular image exists on the transillumination observation image being input, an operation of setting, as a reference area, an area corresponding to the first area on the fluorescence observation image being input, and an operation of obtaining fluorescence intensity data of a fluorescence image from the reference area in the fluorescence observation image.

Further, a computer readable storage medium of the present application being a storage medium capable of being read by a computer of an evaluation apparatus that measures and evaluates a fluorescence intensity of a cellular image, the computer readable storage medium including an input step of inputting a fluorescence observation image of a fluorescent object population and a transillumination observation image having a same field of view as the fluorescence observation image, a first detecting step of detecting, as a first area, an area in which a cellular image exists on the transillumination observation image being input, a setting step of setting, as a reference area, an area corresponding to the first area on the fluorescence observation image being input, and an obtaining step of obtaining fluorescence intensity data of a fluorescence image from the reference area in the fluorescence observation image.

DETAILED DESCRIPTION OF THE EMBODIMENTS

First Embodiment

Hereinafter, a first embodiment of the present application will be described. The present embodiment is an embodiment of an image cytometer.

First, a configuration of the image cytometer will be described.

Figure 1:
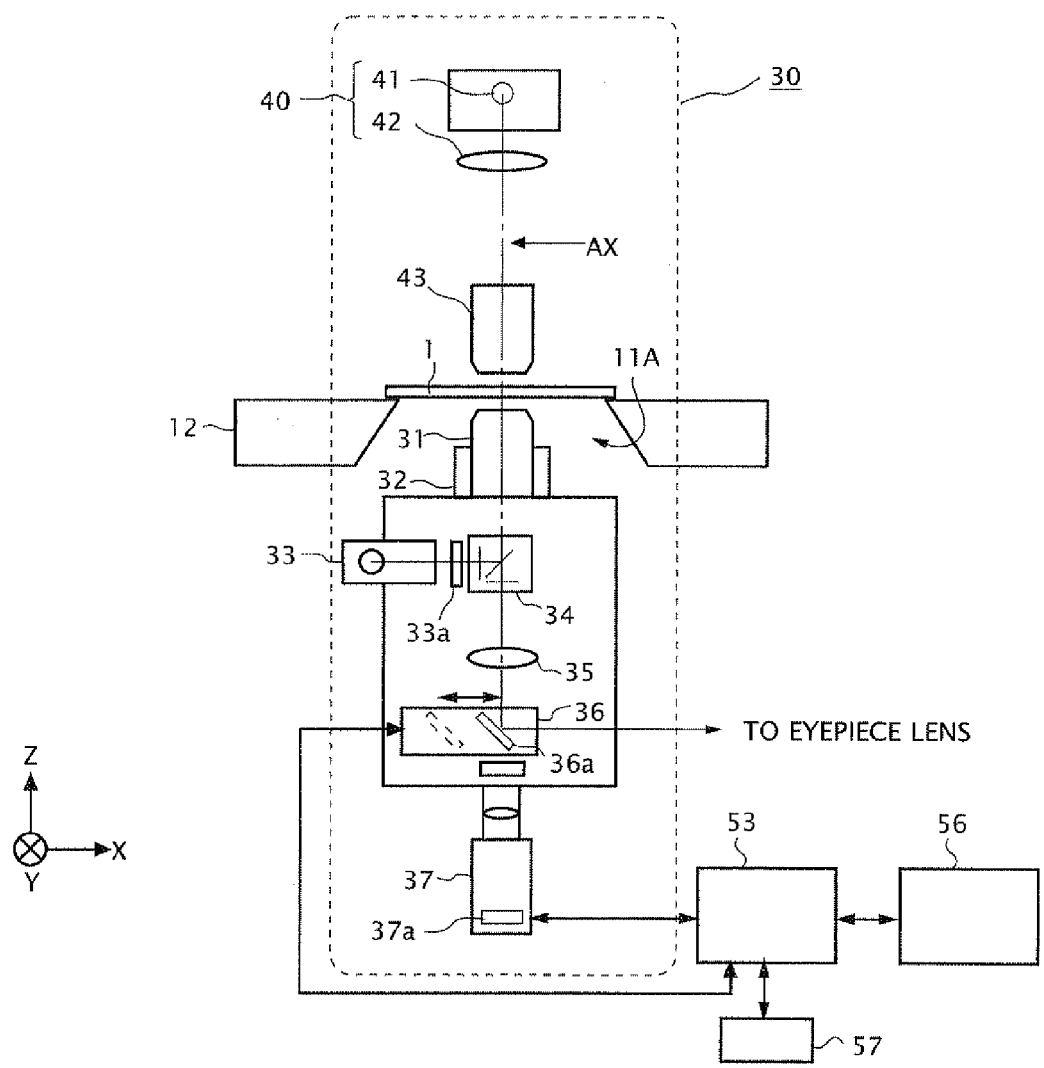
FIG. 1 is an entire configuration diagram of an image cytometer.

FIG. 1 is an entire configuration diagram of the image cytometer. As illustrated in FIG. 1, the image cytometer includes: a two-dimensional mechanical stage 12; a microscope apparatus 30; a computer 53; a displaying device 56; and an input device 57.

An apertural part 11A is provided on a center of the two-dimensional mechanical stage 12, and a sample 1 is placed so as to cover the apertural part 11A. The sample 1 is, for example, a slide glass, and a solution containing cell population stained by a fluorescence-emitting dye is previously dropped on a center of the glass. Note that for the prevention of drying, a surface of the solution is covered with a cover glass. Incidentally, a surface on which the solution is dropped is a lower surface of the slide glass.

Note that in this case, by assuming a case where a cell population whose expression level of EGFP (fluorescence protein) varies is evaluated, a case where a surface antigen of individual cells included in a cell population is detected using a fluorescence antibody method or the like, at least two types of cell groups having different fluorescence intensities are assumed to be included in the cell population in the sample 1.

The microscope apparatus 30 includes: an objective lens 31; a focusing mechanism 32; an excitation light illuminating unit 33; a fluorescence filter block 34; a secondary objective lens 35; a light path switching device 36; an imaging unit 37; a transillumination unit 40; and a condenser lens 43. Among the above, the transillumination unit 40 and the condenser lens 43 are disposed above the sample 1, and the other elements are disposed below the sample 1. Further, the fluorescence filter block 34 is equipped with a dichroic mirror, an excitation filter, a fluorescence filter and the like, and the light path switching device 36 is provided with a mirror 36a which can be inserted into or retracted from a light path.

The objective lens 31 is an objective lens having a relatively wide field of view (objective lens of four magnifications, for example). The objective lens 31 can be moved in a direction of optical axis AX (Z direction) by the focusing mechanism 32. By the movement, focusing of the objective lens 31 with respect to the sample 1 is performed.

The two-dimensional mechanical stage 12 can move in an X direction and a Y direction being directions perpendicular to the optical axis AX. By the movement, positional adjustment of the field of view of the objective lens 31 (observing area) in the sample 1 is conducted.

The transillumination unit 40 can radiate a luminous flux of illumination light for bright-field observation (a reference numeral 41 denotes a light source, and a reference numeral 42 denotes a collimator lens). The transillumination unit 40 is turned on when the bright-field observation is performed, and is turned off when fluorescence observation is performed.

The excitation light illuminating unit 33 can radiate a luminous flux of excitation light for fluorescence observation. The excitation light illuminating unit 33 is turned on when the fluorescence observation is performed, and is turned off when the bright-field observation is performed.

When the bright-field observation is performed, the luminous flux of illumination light emitted from the transillumination unit 40 passes through the condenser lens 43, and illuminates the observing area on the sample 1. The luminous flux transmitted through the sample 1 is incident on the objective lens 31. The luminous flux incident on the objective lens 31 passes through the fluorescence filter block 34 and the secondary objective lens 35, and is incident on the light path switching device 36. When the mirror 36a of the light path switching device 36 is inserted into the light path, the luminous flux is reflected by the mirror 36a to be introduced into a not-illustrated eyepiece lens, and when the mirror 36a of the light path switching device 36 is retracted from the light path, the luminous flux passes through the light path switching device 36 to be incident on the imaging unit 37. The luminous flux incident on the imaging unit 37 forms a bright-field image of the aforementioned observing area on an imaging device 37a in the imaging unit 37. The imaging device 37a captures the bright-field image to obtain image data (referred to as "transillumination image", hereinafter).

When the fluorescence observation is performed, the luminous flux of excitation light emitted from the excitation light illuminating unit 33 passes through a light control filter 33a and the fluorescence filter block 34 to be incident on the objective lens 31 from an image side, and then irradiates the observing area on the sample 1 via the objective lens 31. A fluorescence generated in the sample 1 in accordance with the luminous flux of excitation light is incident on the objective lens 31 from an object side, passes through the fluorescence filter block 34 and the secondary objective lens 35, and is incident on the light path switching device 36. When the mirror 36a of the light path switching device 36 is inserted into the light path, the luminous flux is reflected by the mirror 36a to be introduced into the not-illustrated eyepiece lens, and when the mirror 36a of the light path switching device 36 is retracted from the light path, the luminous flux passes through the light path switching device 36 to be incident on the imaging unit 37. The luminous flux incident on the imaging unit 37 forms a fluorescence image of the aforementioned observing area on the imaging device 37a in the imaging unit 37. The imaging device 37a captures the fluorescence image to obtain image data (referred to as "fluorescence image", hereinafter).

The computer 53 has a control function for controlling the two-dimensional mechanical stage 12 and respective driving parts (the transillumination unit 40, the focusing mechanism 32, the excitation light illuminating unit 33, the light path switching device 36 and the like) of the microscope apparatus 30. By conducting the control, the computer 53 can adjust the position of the observing area on the sample 1, perform switching between the fluorescence observation and the bright-field observation, and perform switching between visual observation and image observation, for example.

Further, the computer 53 has an information processing function for processing the images (the fluorescence image and the transillumination image) obtained by the microscope apparatus 30. For instance, the computer 53 can acquire the images (the fluorescence image and the transillumination image) from the microscope apparatus 30 to store them in a frame memory inside the computer 53, obtain statistical data of the cell population in the aforementioned observing area based on those images, and display the statistical data on the displaying device 56.

Note that an operation of the computer 53 is conducted in accordance with an instruction from a user input through the input device 57. Further, a program required for the operation is previously installed in the computer 53. The installation can be performed via a storage medium, or can also be conducted through a communication network such as Internet.

Next, an operation flow of the computer 53 will be described.

Figure 2:
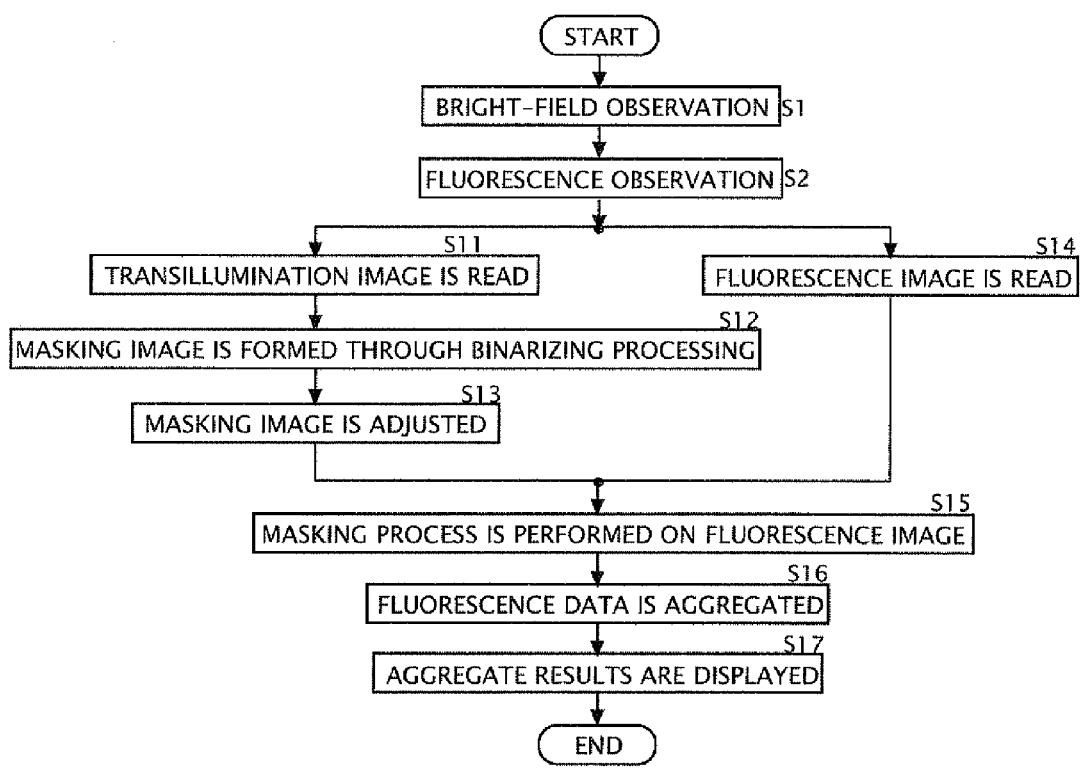
FIG. 2 is an operation flow chart of a computer 53 in a first embodiment.
Figure 3:
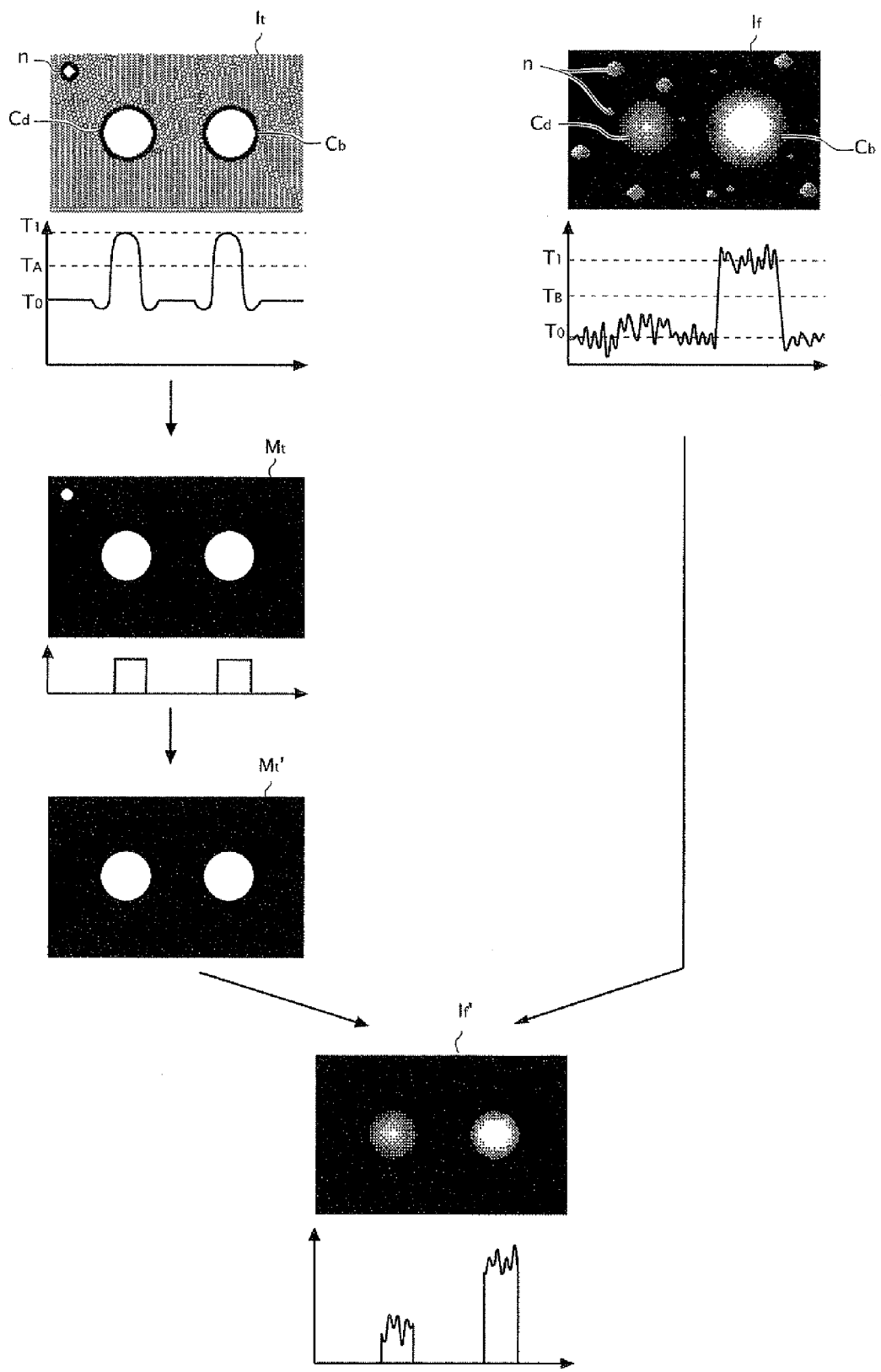
FIG. 3 is a schematic diagram of respective images generated in the first embodiment.

FIG. 2 is an operation flow chart of the computer 53 in the present embodiment, and FIG. 3 is a schematic diagram of images generated in respective steps. Hereinafter, the respective steps will be described in order, while referring to FIG. 2 and FIG. 3.

Step S1: The computer 53 makes the microscope apparatus 30 execute the bright-field observation, acquires a transillumination image It obtained through the bright-field observation from the microscope apparatus 30, and stores the image in the frame memory.

Step S2: The computer 53 makes the microscope apparatus 30 execute the fluorescence observation, acquires a fluorescence image If obtained through the fluorescence observation from the microscope apparatus 30, and stores the image in the frame memory. The fluorescence image If is an image having the same field of view as the transillumination image It obtained in step S1.

In FIG. 3, one cellular image Cb exhibiting strong fluorescence intensity and one cellular image Cd exhibiting weak fluorescence intensity, are assumed to exist on each image (the number of cellular images is actually several tens to several tens of thousands). Note that an image denoted by a reference letter n is a noise.

Further, below each of the images in FIG. 3, there is illustrated a brightness distribution graph on a straight line crossing each of the images (if the number of bits of the aforementioned imaging unit 37 is set as 12, for example, a brightness value of each pixel of each of the images takes any value of 0 to 4095).

As is apparent from the brightness distribution graphs, although the brightness values of both the cellular image Cb exhibiting strong fluorescence intensity and the cellular image Cd exhibiting weak fluorescence intensity are sufficiently higher than a background level (noise level) $T_0$ on the transillumination image It, the brightness value of the cellular image Cd exhibiting weak fluorescence intensity is buried in the background level (noise level) $T_0$ on the fluorescence image If.

Further, although not illustrated in FIG. 3, the background level $T_0$ of the transillumination image It is substantially uniform, but, the background level $T_0$ of the fluorescence image If is likely to be non-uniform.

Accordingly, although it is not possible to correctly distinguish, based only on the fluorescence image If, between the cellular images Cb, Cd and the noise n which exist on the fluorescence image If, it is possible to correctly distinguish between the cellular images Cb, Cd and the noise n which exist on the fluorescence image If, based on the transillumination image It.

Step S11: The computer 53 reads the transillumination image It stored in the frame memory.

Step S12: The computer 53 performs binarizing processing on the transillumination image It, thereby forming a masking image Mt.

As illustrated in FIG. 3, an apertural pattern of the masking image Mt almost matches a distribution pattern of the cellular images Cb, Cd that exist on the transillumination image It (a brightness value of a masking part and a brightness value of an apertural part take 0 and 255, 0 and 65535, or 0 and 1, depending on a software, but, since all of the above combinations are essentially the same, the values are set as 0 and 1, in this case).

In order to obtain such a masking image Mt, a threshold value $T_A$ for the binarizing processing in the present step has to be set to a value which is sufficiently higher than the background level $T_0$ of the transillumination image It and is also sufficiently lower than a cellular brightness value $T_1$ of the transillumination image It.

Accordingly, the computer 53 in the present step forms a brightness histogram of the transillumination image It in advance of the binarizing processing, in which a brightness value that gives a peak on a low brightness side of the brightness histogram is regarded as the background level $T_0$, a maximum brightness value of the brightness histogram is regarded as the cellular brightness value $T_1$, and a value between the background level $T_0$ and the cellular brightness value $T_1$ (intermediate value, for instance) is set as the threshold value $T_A$. By setting the threshold value as described above, it is possible to make the apertural pattern of the masking image Mt almost match the distribution pattern of the cellular images Cb, Cd that exist on the transillumination image It.

However, the apertural pattern of the masking image Mt does not always completely match the distribution pattern of the cellular images Cb, Cd that exist on the transillumination image It. This is because the noise n (which is an image of a bubble, dust, or the like) also exists on the transillumination image It, and there is also a possibility that a brightness value of the noise n is higher than the threshold value $T_A$.

Step S13: In order to remove an unnecessary apertural part on the masking image Mt, the computer 53 adjusts the masking image Mt in a manner as described below.

First, the computer 53 refers to a size and a shape of each of the apertural parts formed on the masking image Mt, and finds out the apertural part in which at least either the size or the shape is abnormal (apertural part whose size or shape is obviously different from a size or a shape of the cellular image). Subsequently, the computer 53 replaces the apertural part with the masking part, to thereby obtain an adjusted masking image Mt'. An apertural pattern of the adjusted masking image Mt' completely matches the distribution pattern of the cellular images Cb, Cd that exist on the transillumination image It.

Note that in the present step, a criterion for judging whether or not the size of the apertural part is abnormal is desirably set in accordance with an observation condition (observation magnification) of the microscope apparatus 30, and a judgment whether or not the shape of the apertural part is abnormal is desirably performed based on a degree of deviation from a perfect circle.

Step S14: The computer 53 reads the fluorescence image If stored in the frame memory.

Step S15: The computer 53 performs Masking process on the fluorescence image If using the masking image Mt', to thereby obtain a masking-processed fluorescence image If'. As illustrated in FIG. 3, the masking-processed fluorescence image If' corresponds to a logical multiplication between the masking image Mt' and the fluorescence image If, in which the noise n generated in the background of the fluorescence image If is completely removed.

Step S16: The computer 53 recognizes position coordinates of individual apertural parts formed on the masking image Mt', and sets ROIs to respective areas corresponding to those apertural parts on the fluorescence image If'. Subsequently, the computer 53 extracts, from the individual ROIs set on the fluorescence image If', fluorescence data such as a brightness maximum value, a brightness average value and a brightness integral value.

Here, since the individual ROIs include not only the fluorescence data but also the background level $T_0$ of the fluorescence image If, the computer 53 forms a brightness histogram of the fluorescence image If in advance of the extraction of the fluorescence data, in which a brightness value that gives a peak on a low brightness side of the brightness histogram is regarded as the background level $T_0$, and the background level $T_0$ is subtracted from each of the ROIs.

Note that the background level $T_0$ of the fluorescence image If is non-uniform, as described above. Accordingly, it is desirable that the computer 53 performs the calculation of background level $T_0$ for each of partial areas formed by plurally dividing the fluorescence image If.

Thereafter, the computer 53 extracts the respective pieces of fluorescence data (the brightness maximum value, the brightness average value, the brightness integral value and the like) from all of the ROIs, and then it forms, based on those pieces of fluorescence data, a histogram of the brightness maximum values, a histogram of the brightness average values, and a histogram of the brightness integral values, as aggregate results. A vertical axis of each of the histograms represents the number of ROIs, namely, the number of cells.

Step S17: The computer 53 displays the formed respective histograms, together with the masking-processed fluorescence image If', on the displaying device 56. Accordingly, the flow is completed.

As described above, the computer 53 of the present embodiment forms the masking image Mt' used in the masking process, based on the transillumination image It having the same field of view as the fluorescence image If.

Although the transillumination image It does not include the fluorescence data of the cellular images Cb, Cd at all, it has a high SN ratio and a uniform background level $T_0$, different from the fluorescence image If. Accordingly, with the use of the masking image Mt' formed in the present embodiment, it is possible to securely eliminate a possibility of accidentally removing the cellular images Cb, Cd and a possibility that the noise n remains.

Therefore, according to the image cytometer of the present embodiment, it is possible to obtain the statistical data of the cell population with high accuracy.

Note that although the computer 53 of the present embodiment automatically performs the calculation of background level $T_0$ of each of the transillumination image It, the fluorescence image If and the partial areas, the calculation of background level $T_0$ regarding at least one of the transillumination image, the fluorescence image and the partial areas can also be performed semi-automatically.

In that case, the computer 53 is only required to display the image being a calculation target of the background level $T_0$ on the displaying device 56, make a user specify, on the display screen, a background window with any shape and any size, and to regard a brightness average value in the specified background window as the background level $T_0$ of the image.

Second Embodiment

Hereinafter, a second embodiment of the present application will be described. The present embodiment is also an embodiment of the image cytometer. Here, description is made only on a point different from the first embodiment.

Although description is not made in the first embodiment, on the fluorescence image If, the cellular image Cb exhibiting strong fluorescence intensity tends to expand, compared to the cellular image Cd exhibiting weak fluorescence intensity. Besides, the degree of expansion has a strong correlation with the fluorescence intensity.

However, since the computer 53 of the first embodiment uses the masking image Mt' formed only from the transillumination image It for the masking process, an expanded portion (surrounding edge portion) of the cellular image Cb exhibiting strong fluorescence intensity is removed together with the noise n. In this case, fluorescence data of the expanded portion is not reflected on the aggregate results, so that a certain error occurs in the aggregate results.

Accordingly, the computer 53 of the present embodiment forms a masking image to be used for the masking process, based on both the transillumination image It and the fluorescence image If.

Figure 4:
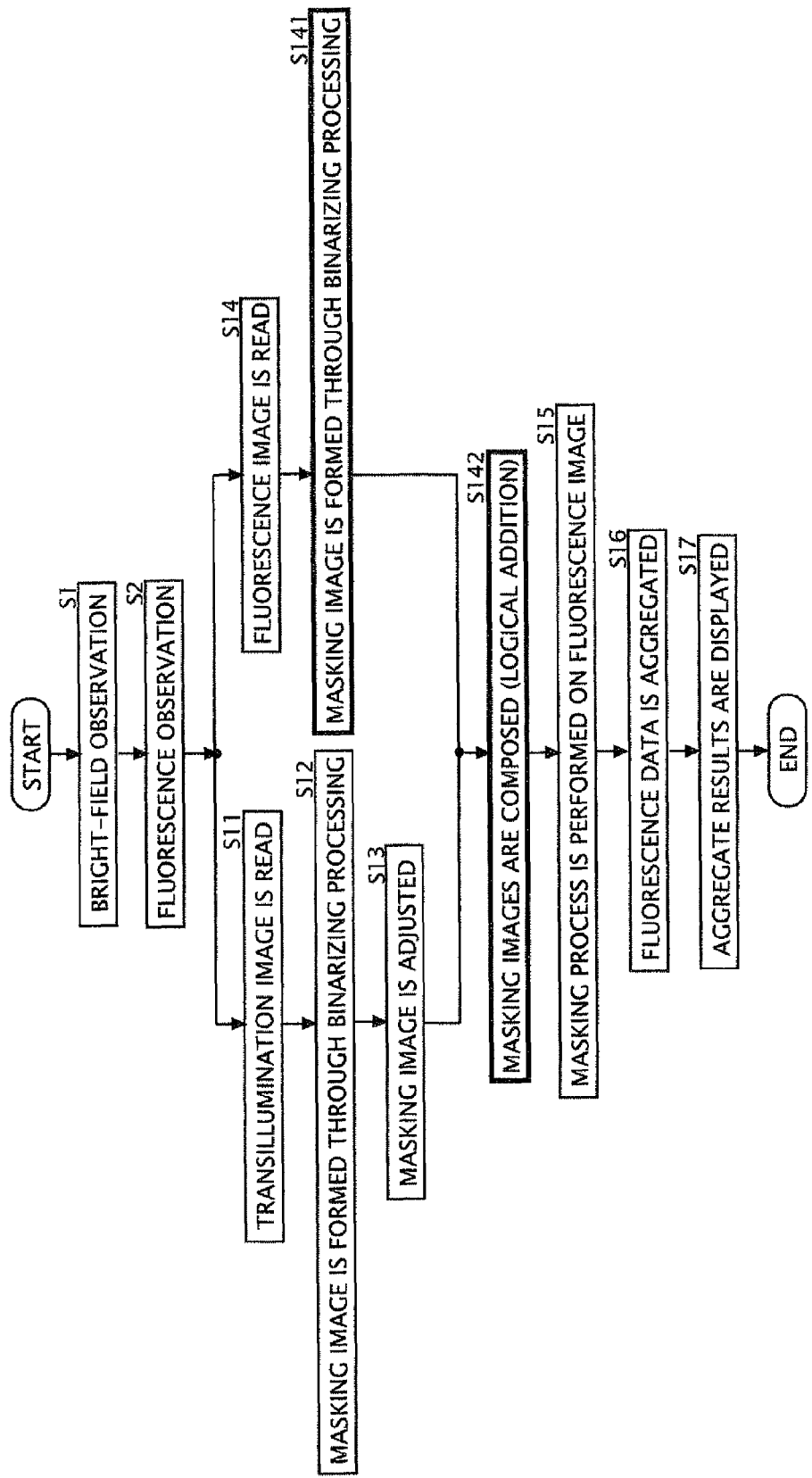
FIG. 4 is an operation flow chart of the computer 53 in a second embodiment.
Figure 5:
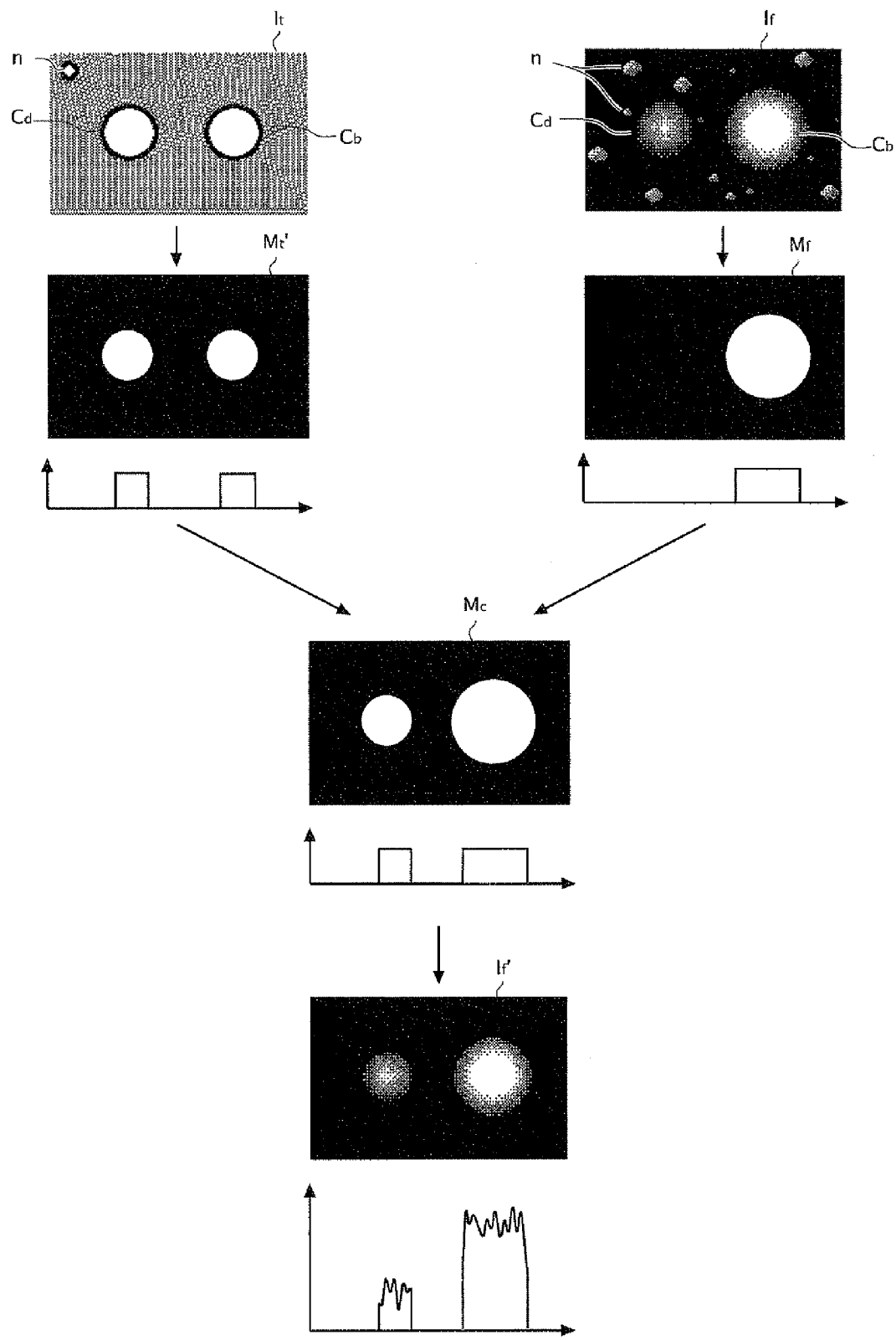
FIG. 5 is a schematic diagram of respective images generated in the second embodiment.

FIG. 4 is an operation flow chart of the computer 53 in the present embodiment, and FIG. 5 is a schematic diagram of images generated in respective steps. In FIG. 4, a point different from FIG. 2 is that step S141 is inserted in a subsequent stage of step S14, and step S142 is inserted in a previous stage of step S15. Hereinafter, steps S141 and S142 will be described in order, while referring to FIG. 4 and FIG. 5.

Step S141: The computer 53 performs binarizing processing on the fluorescence image If, thereby forming a masking image Mf.

As illustrated in FIG. 5, an apertural pattern of the masking image Mf matches a distribution pattern of the cellular image Cb existing on the fluorescence image If and exhibiting strong fluorescence intensity, and an area in which the cellular image Cd existing on the fluorescence image If and exhibiting weak fluorescence intensity exists, is made to be a masking part.

In order to obtain such a masking image Mf, a threshold value $T_B$ for the binarizing processing in the present step has to be set to a value which is sufficiently higher than the background level $T_0$ of the fluorescence image If and is also sufficiently lower than a cellular brightness value $T_1$ of the fluorescence image If.

Accordingly, the computer 53 in the present step forms a brightness histogram of the fluorescence image If in advance of the binarizing processing, in which a brightness value that gives a peak on a low brightness side of the brightness histogram is regarded as the background level $T_0$, a maximum brightness value of the brightness histogram is regarded as the cellular brightness value $T_1$, and a value between the background level $T_0$ and the cellular brightness value $T_1$ (intermediate value, for instance) is set as the threshold value $T_B$. By setting the threshold value as described above, it is possible to make the apertural pattern of the masking image Mf match the distribution pattern of the cellular image Cb existing on the fluorescence image If and exhibiting strong fluorescence intensity.

Step S142: The computer 53 performs logical addition between the masking image Mt' formed from the transillumination image It and the masking image Mf formed from the fluorescence image If, thereby forming a composite masking image Mc. As illustrated in FIG. 5, an apertural pattern of the composite masking image Mc completely matches the distribution pattern of the cellular images Cb, Cd that exist on the fluorescence image If. Further, in the masking process (step S15) of the present embodiment, the composite masking image Mc is used.

Therefore, according to the masking process of the present embodiment, there is no chance that the expanded portion of the cellular image Cb is missed from the fluorescence image If. Accordingly, in the present embodiment, an accuracy of aggregate results becomes better than that of the first embodiment.

Third Embodiment

Hereinafter, a third embodiment of the present application will be described. The present embodiment is also an embodiment of the image cytometer. Here, description is made only on a point different from the second embodiment.

Figure 7:
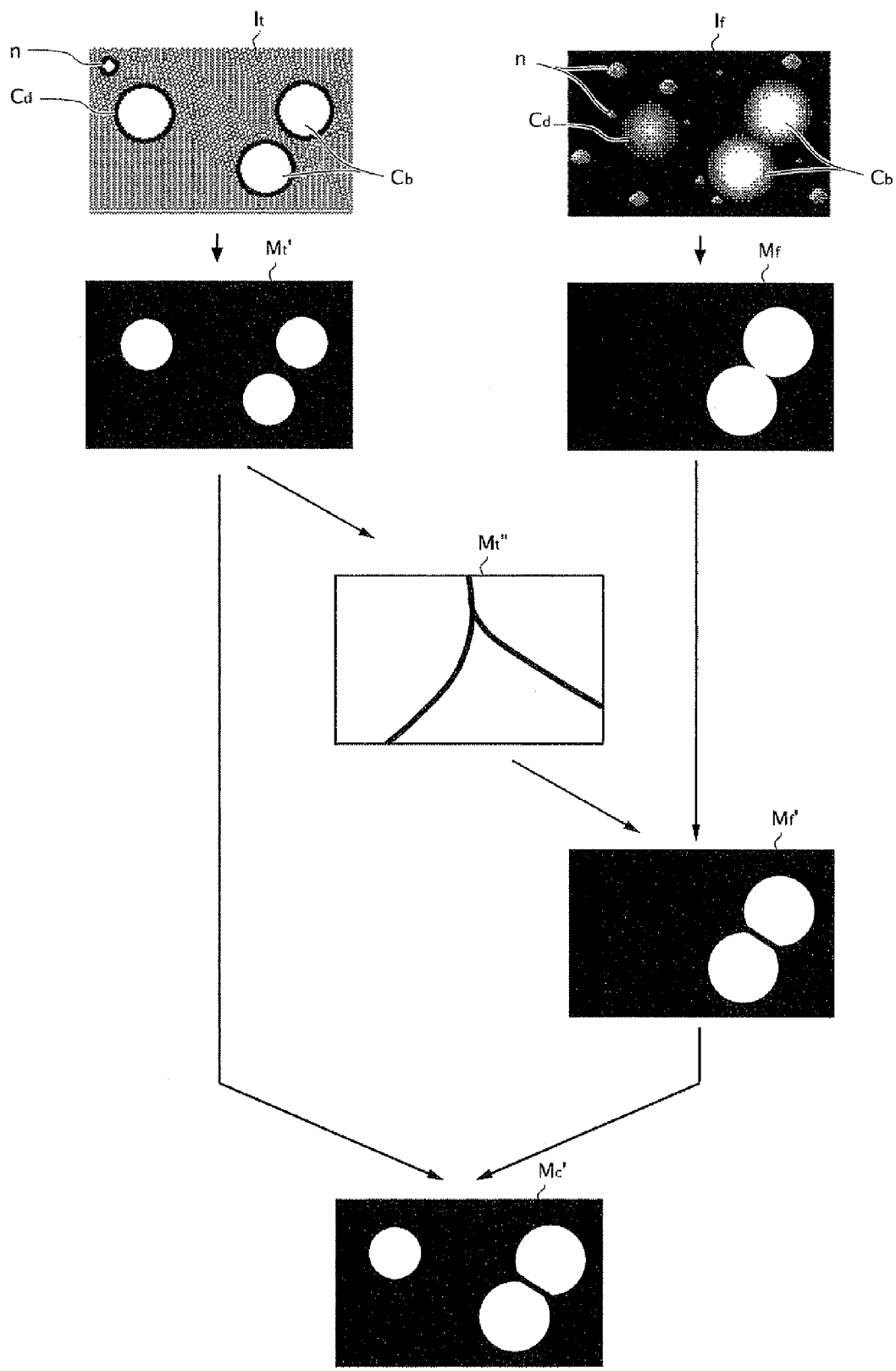
FIG. 7 is a schematic diagram of respective images generated in the third embodiment.

Although description is not made in the second embodiment, when, as illustrated in FIG. 7, two cellular images Cb exhibiting strong fluorescence intensity exist close to each other on the fluorescence image If, two apertural parts corresponding to those cellular images Cb sometimes coalesce on the masking image Mf formed from the fluorescence image If. In that case, fluorescence data of those cellular images Cb is aggregated as fluorescence data of one cellular image, so that an error occurs in the aggregate results.

Accordingly, the computer 53 of the present embodiment adjusts the masking image Mf formed from the fluorescence image If.

Figure 6:
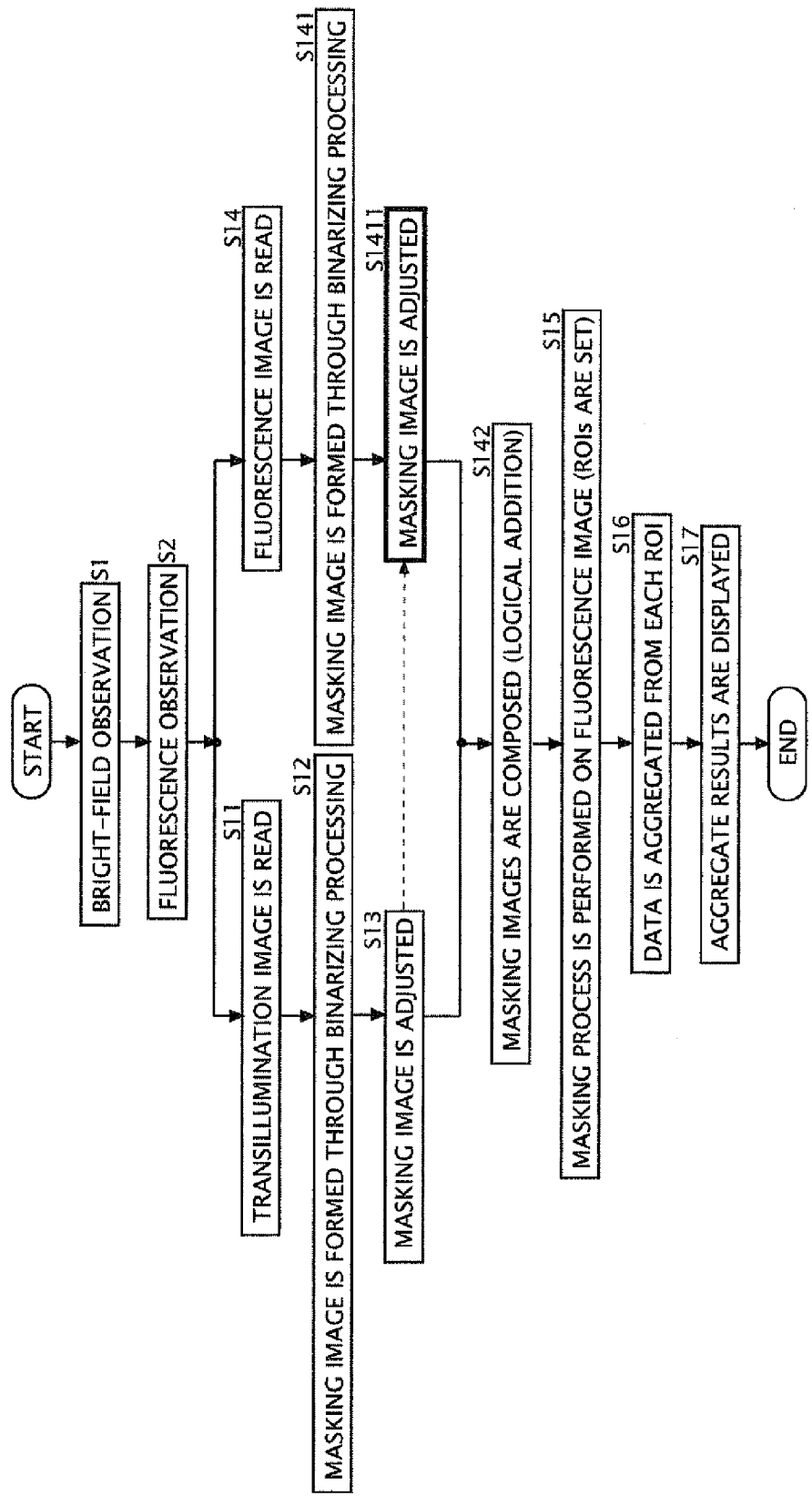
FIG. 6 is an operation flow chart of the computer 53 in a third embodiment.

FIG. 6 is an operation flow chart of the computer 53 in the present embodiment, and FIG. 7 is a schematic diagram of images generated in respective steps. In FIG. 6, a point different from FIG. 4 is that step S1411 is inserted in a subsequent stage of step S141. Hereinafter, the inserted step S1411 will be described.

Step S1411: The computer 53 adjusts, based on the masking image Mt' formed from the transillumination image It, the masking image Mf formed from the fluorescence image If in a manner as described below.

First, the computer 53 calculates a borderline between the apertures formed on the masking image Mt', and forms a temporally masking image Mt" having an apertural pattern same as the borderline pattern. Further, the computer 53 performs logical multiplication between the temporally masking image Mt" and the masking image Mf, to thereby obtain an adjusted masking image Mf'.

As illustrated in FIG. 7, the number and disposition relationship of apertural parts formed on the adjusted masking image Mf' completely match the number and disposition relationship of the cellular images Cb existing on the fluorescence image If and exhibiting strong fluorescence intensity.

Further, in masking composition (step S142) of the present embodiment, the adjusted masking image Mf' is used instead of the masking image Mf.

Therefore, as illustrated in FIG. 7, in a composite masking image Mc' of the present embodiment, the number and disposition relationship of apertural parts completely match the number and disposition relationship of the cellular images Cb, Cd that exist on the transillumination image It. Accordingly, in the present embodiment, an accuracy of aggregate results becomes better than that of the second embodiment.

[Other Features]

Note that in either of the aforementioned embodiments, a bright-field observation method is applied as an observation method at the time of obtaining the transillumination image It, but, it is also possible to apply another transillumination observation method such as a phase contrast observation method, a differential interference contrast observation method and a polarized light observation method.

Further, in either of the aforementioned embodiments, description is made on a case where the cellular brightness value $T_1$ in the transillumination image It is higher than the background level $T_0$, but, depending on a combination of the types of cells and the types of observation methods, the cellular brightness value $T_1$ sometimes becomes lower than the background level $T_0$. In that case, there is a need to perform reversal processing on the masking image Mt formed from the transillumination image It.

Further, in either of the aforementioned embodiments, description is made on a case where the cellular brightness value $T_1$ in the transillumination image It is different from the background level $T_0$, but, depending on a combination of the types of cells and the types of observation methods, the cellular brightness value $T_1$ sometimes becomes nearly equal to the background level $T_0$. In that case, it is only required to set the threshold value $T_A$ based on a brightness value of an edge of the cellular image instead of the cellular brightness value $T_1$. However, in that case, the apertural part on the masking image Mt takes, not a planar shape but a closed curve shape, so that there is a need to perform processing for replacing the inside of the closed curve with the apertural part, on the masking image Mt.

Further, in either of the aforementioned embodiments, the cell population stained by the fluorescence-emitting dye is set as an evaluation target, but, it is also possible to set another particulate fluorescent object population such as, for example, plastic or glass beads, liposomes and liquid drops, as evaluation targets.

EXAMPLE 1

Hereinafter, an example corresponding to the aforementioned second embodiment will be described.

First, a thymocyte cell line BW5147 was previously prepared. Further, a plasmid DNApMRX-IRES-EGFP containing a gene of fluorescence protein EGFP was introduced into a retrovirus packaging cell Plat-E, and a culture supernatant containing retrovirus produced by the cell was collected. The previously prepared thymocyte cell line BW5147 was infected by the culture supernatant. Further, the infected BW5147 cells were subjected to a flow cytometer, thereby extracting only the BW5147 cells exhibiting the EGFP. Hereinafter, the extracted cell population is called as "cell population exhibiting strong fluorescence intensity".

Meanwhile, there was prepared a cell population into which the plasmid was not introduced. Hereinafter, the cell population is called as "cell population exhibiting weak fluorescence intensity".

Thereafter, the cell population exhibiting strong fluorescence intensity and the cell population exhibiting weak fluorescence intensity were separately incubated in the same type of medium. The medium is RPMI 1640 containing 10% fetal calf serum (FCS), 50μ M2-mercaptoethanol, 10 mM HEPES, 2 mM L-glutamine, 1× nonessential amino acids, 1 mM sodium pyruvate, 100 U/mL penicillin, and 100 μg/mL streptomycin. Further, an incubation apparatus used for the incubation was an incubator in which a temperature was set to 37° C. and a $CO_2$ concentration was set to 5%.

After the incubation, one drop of mixed solution in which the cell population exhibiting strong fluorescence intensity and the cell population exhibiting weak fluorescence intensity were mixed, was dropped on a slide glass and covered with a cover glass, which was prepared as a sample, and the sample was placed, with its cover glass surface down, on a two-dimensional mechanical stage of an inverted microscope (Nikon TE2000-E).

A condenser lens used in the inverted microscope was LWD condenser, and an objective lens used in the inverted microscope was Plan Apo 4× having a numerical aperture of 0.2.

Further, an excitation light illuminating unit used in the inverted microscope was an Intensilight fiber light source, and a fluorescence filter block used in the inverted microscope was one in which EX465-495 as an excitation filter, DM505 as a dichroic mirror, and BA515-555 as a fluorescence filter were combined.

Further, a camera of an imaging unit used in the inverted microscope was a black-and-white camera Ds-Qi1, and NIS-Elements AR 2.3 was used for conducting camera control and image obtaining processing. The number of pixels of the camera was 1280×1000, and the pixel depth was 12 bits.

An exposure time of the camera at the time of bright-field observation and an exposure time of the camera at the time of fluorescence observation were set to about 5 seconds, respectively. Under the setting, the bright-field observation and the fluorescence observation were performed in sequence.

Figure 8:
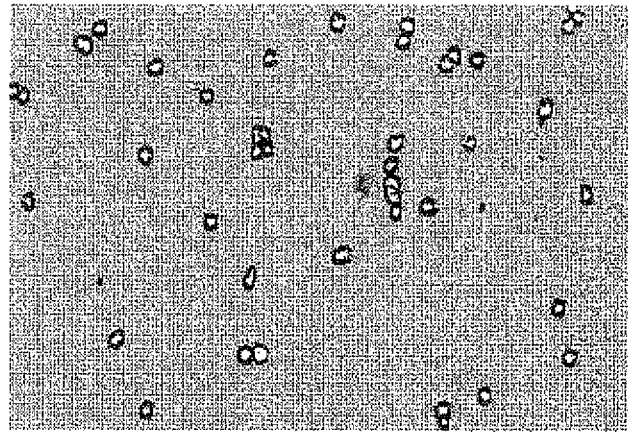
FIG. 8 is (a part of) a transillumination image obtained in an example.
Figure 9:
FIG. 9 is (a part of) a fluorescence image obtained in the example.

A transillumination image (having a tone of 12 bits) obtained through the bright-field observation was as illustrated in FIG. 8, and a fluorescence image (having a tone of 12 bits) obtained through the fluorescence observation was as illustrated in FIG. 9. Note that in FIG. 8, FIG. 9 and respective drawings hereinbelow, a part of each image was enlarged to be illustrated so that cellular images become easy to see.

Subsequently, on the computer, the following processing was performed on the transillumination image and the fluorescence image.

First, binarizing processing was performed on the transillumination image having the tone of 12 bits (FIG. 8). In the binarizing processing, a threshold value was set to 2753, and a pixel having a brightness value exceeding the threshold value was transformed into a pixel having a brightness value of 1, and a pixel having a brightness value equal to or lower than the threshold value was transformed into a pixel having a brightness value of 0. Note that the threshold value 2753 was derived using the following equation.

Threshold value=(4095−background level)×15%+ background level of transillumination image Note that the value 4095 in the equation indicates a brightness maximum value of the camera. A masking image formed as above was as illustrated in FIG. 10.

Next, binarizing processing was performed on the fluorescence image having the tone of 12 bits (FIG. 9). In the binarizing processing, a threshold value was set to 553, and a pixel having a brightness value exceeding the threshold value was transformed into a pixel having a brightness value of 1, and a pixel having a brightness value equal to or lower than the threshold value was transformed into a pixel having a brightness value of 0. Note that the threshold value 553 was derived using the following equation.

Threshold value=(4095−background level)×10%+ background level of fluorescence image Note that the value 4095 in the equation indicates the brightness maximum value of the camera. A masking image formed as above was as illustrated in FIG. 11.

Figure 10:
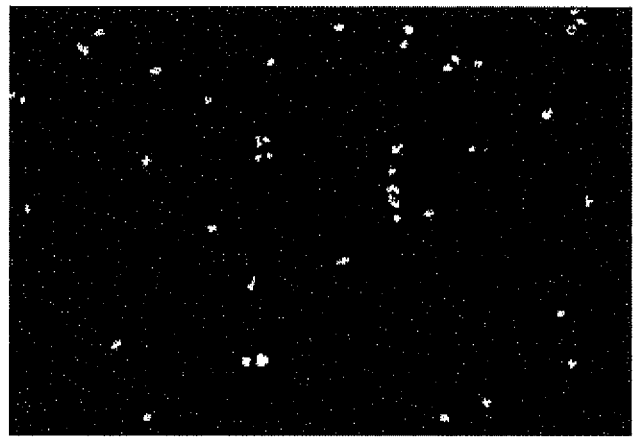
FIG. 10 is (a part of) a masking image formed from the transillumination image in the example.
Figure 11:
FIG. 11 is (a part of) a masking image formed from the fluorescence image in the example.

Next, by performing logical addition between the masking image illustrated in FIG. 10 and the masking image illustrated in FIG. 11, a composite masking image was generated. The generated composite masking image was as illustrated in FIG. 12.

Figure 12:
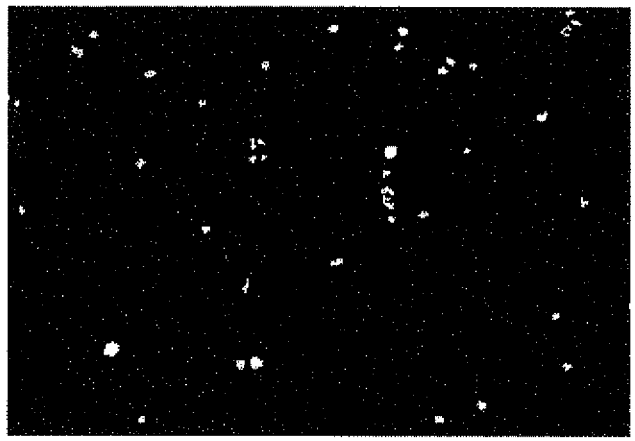
FIG. 12 is (a part of) a composite masking image formed in the example.
Figure 13:
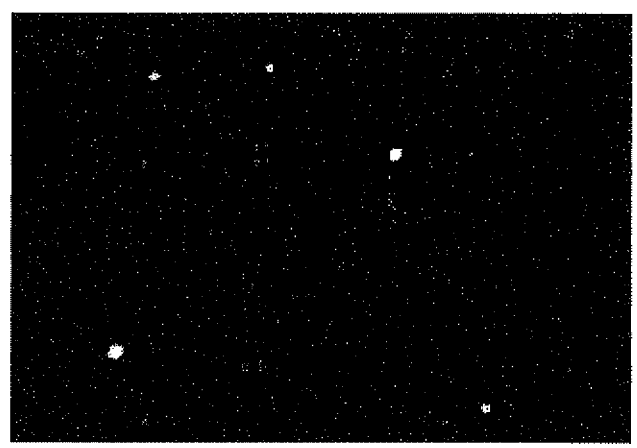
FIG. 13 is (a part of) a masking-processed fluorescence image in the example.

Next, by performing logical multiplication between the composite masking image illustrated in FIG. 12 and the fluorescence image illustrated in FIG. 9, masking process was performed on the fluorescence image. The masking-processed fluorescence image was as illustrated in FIG. 13.

Figure 14:
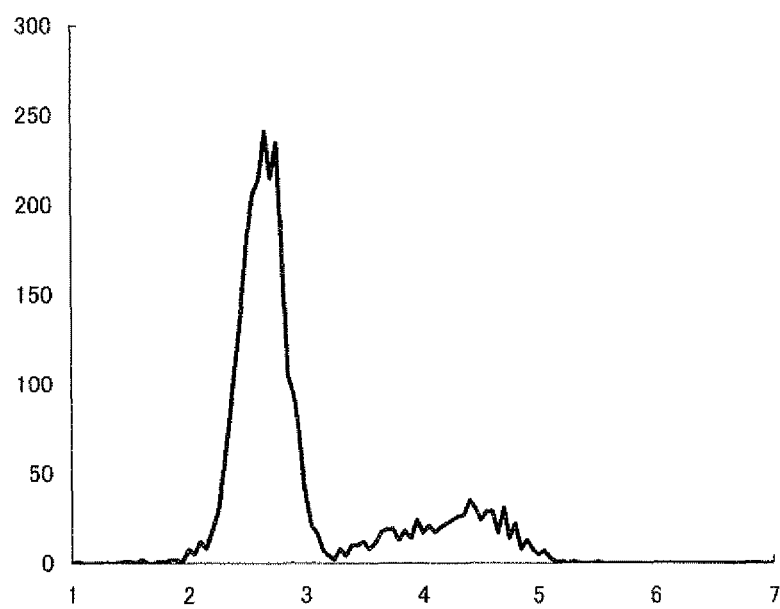
FIG. 14 is a histogram formed in the example.

In the entire masking-processed fluorescence image (FIG. 13), there existed 596 cellular images. Brightness integral values of individual cellular images were calculated, common logarithms (logarithms with base 10) of the brightness integral values were taken, and results thereof were formed as a histogram in increments of 0.05. The formed histogram was as illustrated in FIG. 14.

There are two peaks appeared in the histogram. The reason why the two peaks appeared is that the cell population exhibiting strong fluorescence intensity and the cell population exhibiting weak fluorescence intensity were mixed in the sample.

From the histogram, it can be understood that the number of cells of the cell population exhibiting strong fluorescence intensity was 104, and the number of cells of the cell population exhibiting weak fluorescence intensity was 492.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. An image processing apparatus comprising:
   a storage unit receiving a fluorescence observation image of a cell population stained by a fluorescence dye and a transillumination observation image having a same field of view as the fluorescence observation image;
   a processor configured to:
      specify, by applying a threshold value to the transillumination observation image, a first area group in which an image of the cell population exists in the transillumination observation image;
      set, as a reference area group, an area group corresponding to the first area group in the fluorescence observation image in which a mask is applied to the reference area group; and
      obtain fluorescence intensity data from the reference area group set in the fluorescence observation image.

2. The image processing apparatus according to claim 1, wherein the processor is further configured to:
   generate statistical data from the fluorescence intensity data obtained by the processor.

3. The image processing apparatus according to claim 2, wherein:
   the processor is configured to specify, as a second area group, an area group with a brightness brighter than a predetermined degree in the fluorescence observation image,
   the processor is configured to calculate a logical addition of the first area group and the second area group, and defines an area group corresponding to the logical addition in the fluorescence observation image as the reference area group.

4. The image processing apparatus according to claim 3, wherein:

in advance of the calculation of the logical addition, the processor is configured to calculate a borderline between areas in the first area group, and separate an area positioned on the borderline, among the second area group at the borderline.

5. An image processing method comprising:

receiving a fluorescence observation image of a cell population stained by a fluorescence dye and a transillumination observation image having a same field of view as the fluorescence observation image;

specifying, by applying a threshold value to the transillumination observation image, a first area group in which an image of the cell population exists in the transillumination observation image;

setting, as a reference area group, an area group corresponding to the first area group in the fluorescence observation image in which a mask is applied to the reference area group; and obtaining fluorescence intensity data from the reference area group set in the fluorescence observation image.

6. The image processing method according to claim 5, further comprising:

generating statistical data from the obtained fluorescence intensity data.

7. The image processing method according to claim 6, comprising:

specifying, as a second area group, an area group with a brightness brighter than a predetermined degree in the fluorescence observation image, wherein:

in the step of setting, a logical addition of the first area group and the second area group is calculated, and an area group corresponding to the logical addition in the fluorescence observation image is defined as the reference area group.

8. The image processing method according to claim 7, wherein:

in the step of setting in advance of the calculation of the logical addition, a borderline between areas in the first area group is calculated, and an area positioned on the borderline, among the second area group, is separated at the borderline.

9. A non-transitory computer readable storage medium that stores a computer-executable program, the program comprising instructions for:

receiving a fluorescence observation image of a cell population stained by a fluorescence dye and a transillumination observation image having a same field of view as the fluorescence observation image;

specifying, by applying a threshold value to the transillumination observation image, a first area, an area in which an image of the cell population exists in the transillumination observation image;

setting, as a reference area group, an area group corresponding to the first area group in the fluorescence observation image in which a mask is applied to the reference area group; and obtaining fluorescence intensity data from the reference area group set in the fluorescence observation image.

10. The non-transitory computer readable storage medium according to claim 9, further comprising instructions for:

generating statistical data from the fluorescence intensity data obtained by the obtaining step.

11. The non-transitory computer readable storage medium according to claim 10, the program comprising instructions for:

specifying, as a second area group, an area group with a brightness brighter than a predetermined degree exists in the fluorescence observation image, wherein:

the setting instructions include instructions for calculating a logical addition of the first area group and the second area group, and defining an area group corresponding to the logical addition in the fluorescence observation image as the reference area.

12. The non-transitory computer readable storage medium according to claim 11, wherein:

the setting instructions include instructions for, in advance of the calculation of the logical addition, calculating a borderline between areas in the first area group, and separating an area positioned on the borderline, among the second area group, at the borderline.

13. A microscope system, comprising:

an optical system obtaining the fluorescence observation image;

an optical system obtaining a transillumination observation image having a same field of view as the fluorescence observation image; and the image processing apparatus according to claim 1.

14. A microscope system, comprising:

an optical system obtaining the fluorescence observation image;

an optical system obtaining a transillumination observation image having a same field of view as the fluorescence observation image; and the image processing apparatus according to claim 2.

15. A microscope system, comprising:

an optical system obtaining the fluorescence observation image;

an optical system obtaining a transillumination observation image having a same field of view as the fluorescence observation image; and the image processing apparatus according to claim 3.

16. A microscope system, comprising:

an optical system obtaining the fluorescence observation image;

an optical system obtaining a transillumination observation image having a same field of view as the fluorescence observation image; and the image processing apparatus according to claim 4.

* * * * *